United States Patent [19]

Segal

[11] Patent Number: 5,695,469

[45] Date of Patent: Dec. 9, 1997

[54] VASCULAR DILATATION DEVICE AND METHOD

[76] Inventor: Jerome Segal, 6132 Western Ave., Chevy Chase, Md. 20815

[21] Appl. No.: 569,579

[22] Filed: Dec. 8, 1995

Related U.S. Application Data

[63] Continuation-in-part of Ser. No. 353,558, Dec. 9, 1994, Pat. No. 5,527,282.

[51] Int. Cl.⁶ .................................................. A61M 29/00
[52] U.S. Cl. ........................... 604/104; 604/282; 604/53
[58] Field of Search ................................... 604/104, 282, 604/53, 107, 106; 606/194

[56] References Cited

U.S. PATENT DOCUMENTS

| | | | |
|---|---|---|---|
| 3,996,938 | 12/1976 | Clark, III | 128/303 |
| 4,572,186 | 2/1986 | Gould et al. | 604/105 X |
| 4,581,017 | 4/1986 | Sahota | 604/101 |
| 4,650,466 | 3/1987 | Luther | 604/95 |
| 4,655,771 | 4/1987 | Wallsten | 623/1 |
| 4,723,549 | 2/1988 | Wholey et al. | 604/101 |
| 4,885,003 | 12/1989 | Hillstead | 604/22 |
| 4,921,484 | 5/1990 | Hillstead | 604/104 |
| 5,034,001 | 7/1991 | Garrison et al. | 604/53 |
| 5,061,275 | 10/1991 | Wallsten et al. | 623/1 |
| 5,071,407 | 12/1991 | Termin et al. | 604/104 |
| 5,207,644 | 5/1993 | Strecker | 60/175 |
| 5,344,402 | 9/1994 | Crocker | 604/96 |
| 5,368,566 | 11/1994 | Crocker | 604/101 |
| 5,460,608 | 10/1995 | Lodin et al. | 606/194 X |
| 5,492,532 | 2/1996 | Ryan et al. | 606/194 |

*Primary Examiner*—Michael Powell Buiz
*Assistant Examiner*—N. Kent Gring
*Attorney, Agent, or Firm*—Flehr Hohbach Test Albritton & Herbert LLP

[57] ABSTRACT

A vascular dilatation device for enlarging a flow passage in an obstruction in a vessel carrying flowing blood. A flexible cylindrical dilatation member having first and second ends is placed in the flow passage in the obstruction. An intermediate portion lies between the first and second ends. The flexible cylindrical dilatation member also has an interior flow passage with a diameter and a longitudinally extending central axis extending therethrough. The diameter of the flow passage is variable with movement of the first and second ends relative to each other along the longitudinally extending central axis from a contracted to an expanded condition. A control mechanism causes relative axial movement between the first and second ends towards each other from an extended position to a contracted position. The control mechanism includes an inner flexible elongate tubular member between the first and second ends of the flexible cylindrical dilatation member. The inner flexible elongate tubular member is sufficiently rigid and causes elongation of the cylindrical dilatation member to decrease its diameter and to advance the cylindrical dilatation member through the obstruction in the vessel while preventing axial contraction of the cylindrical dilatation member.

17 Claims, 5 Drawing Sheets

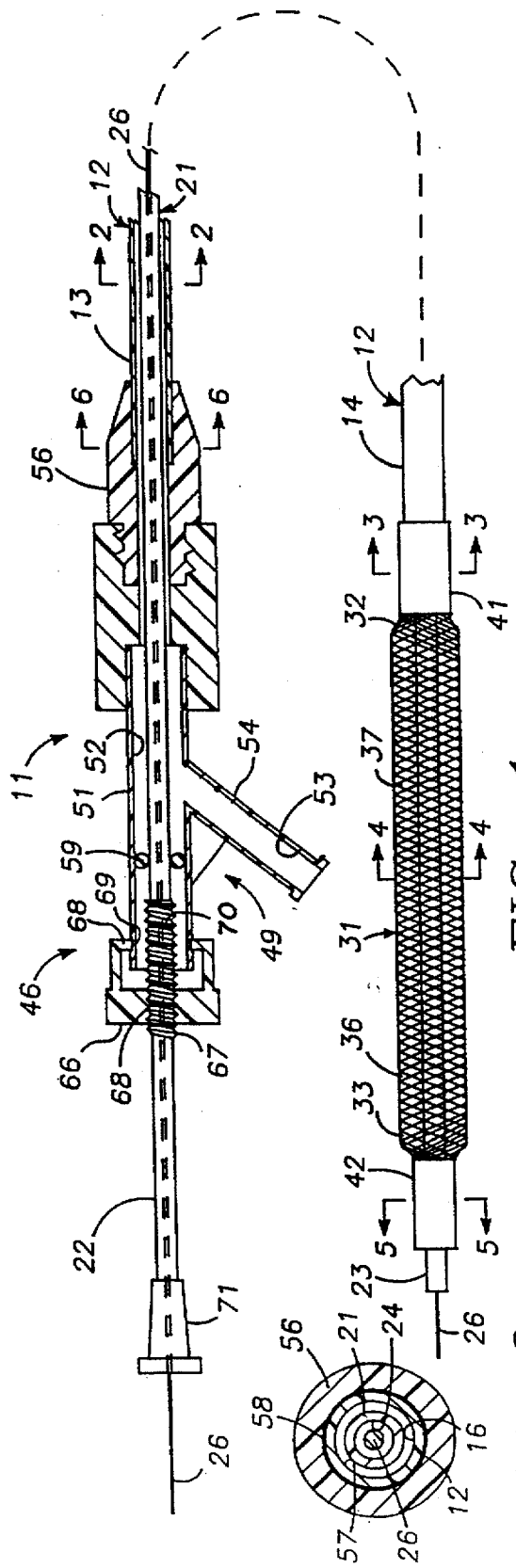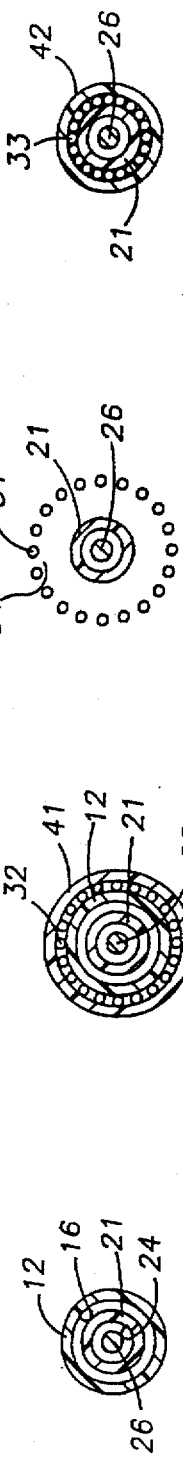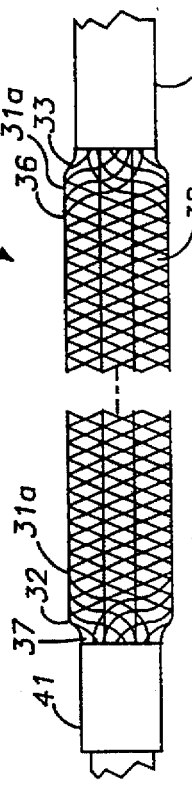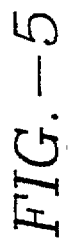

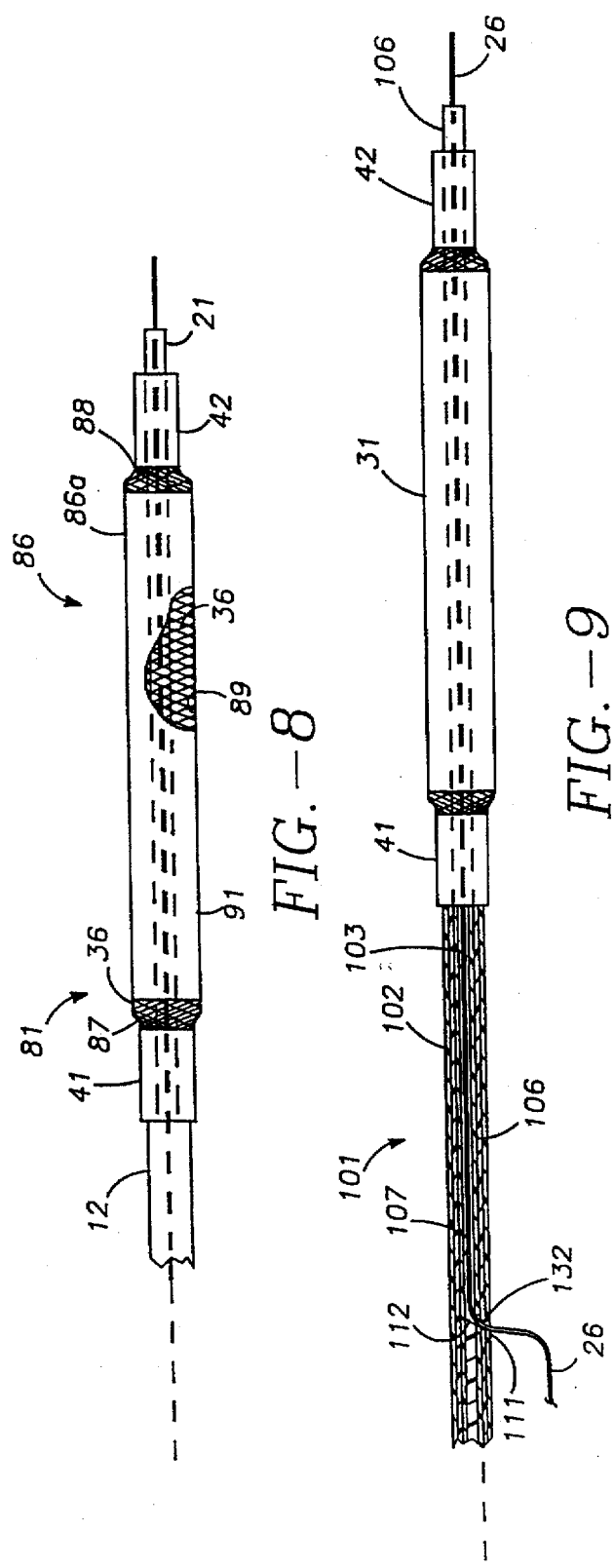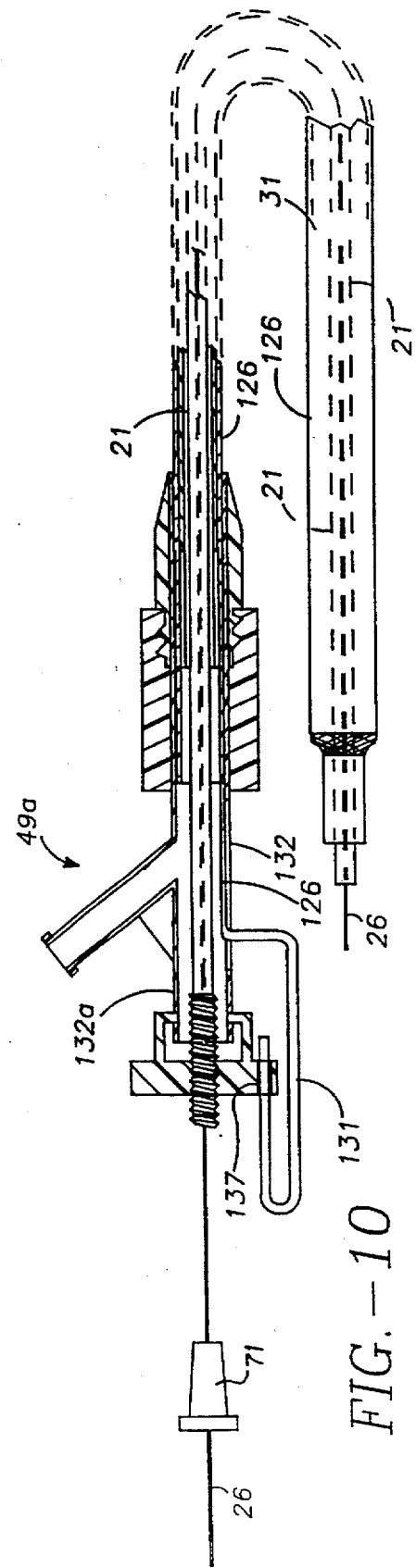

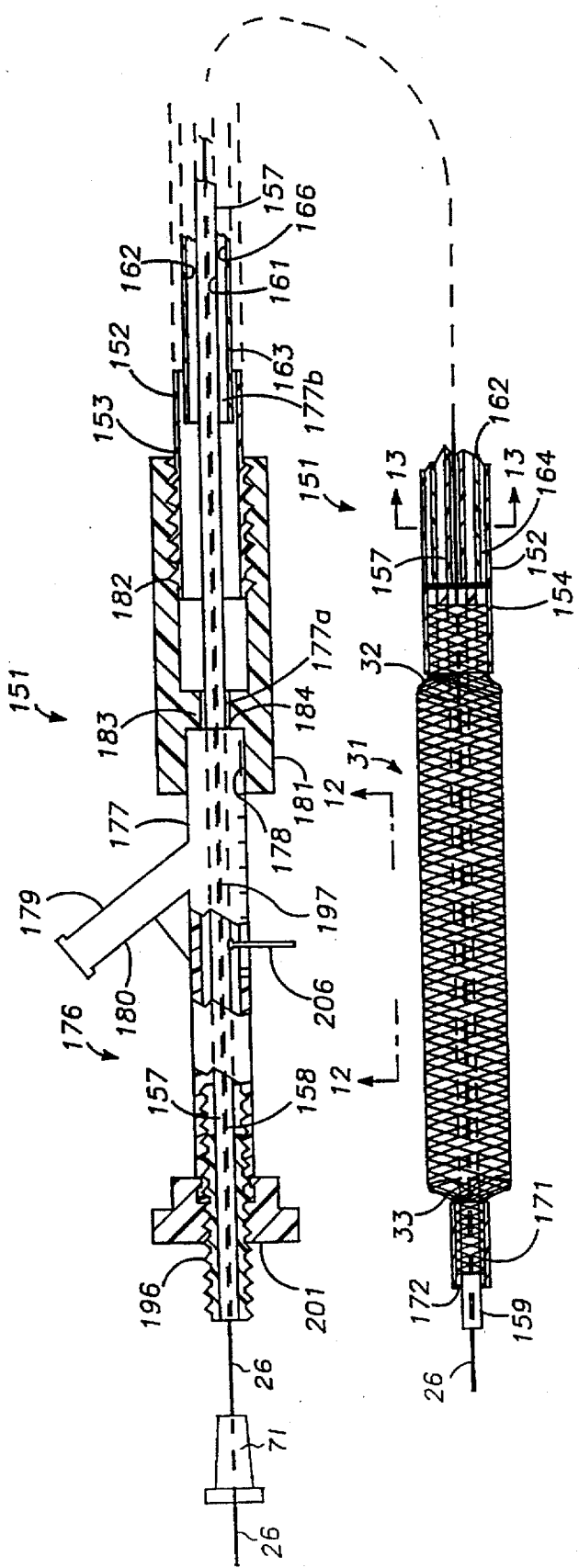
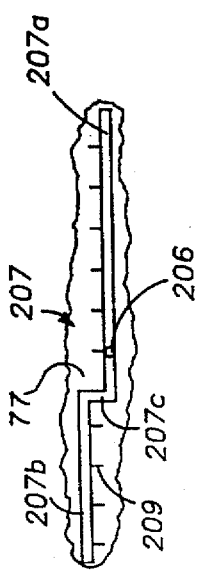
FIG.-11
FIG.-12
FIG.-13

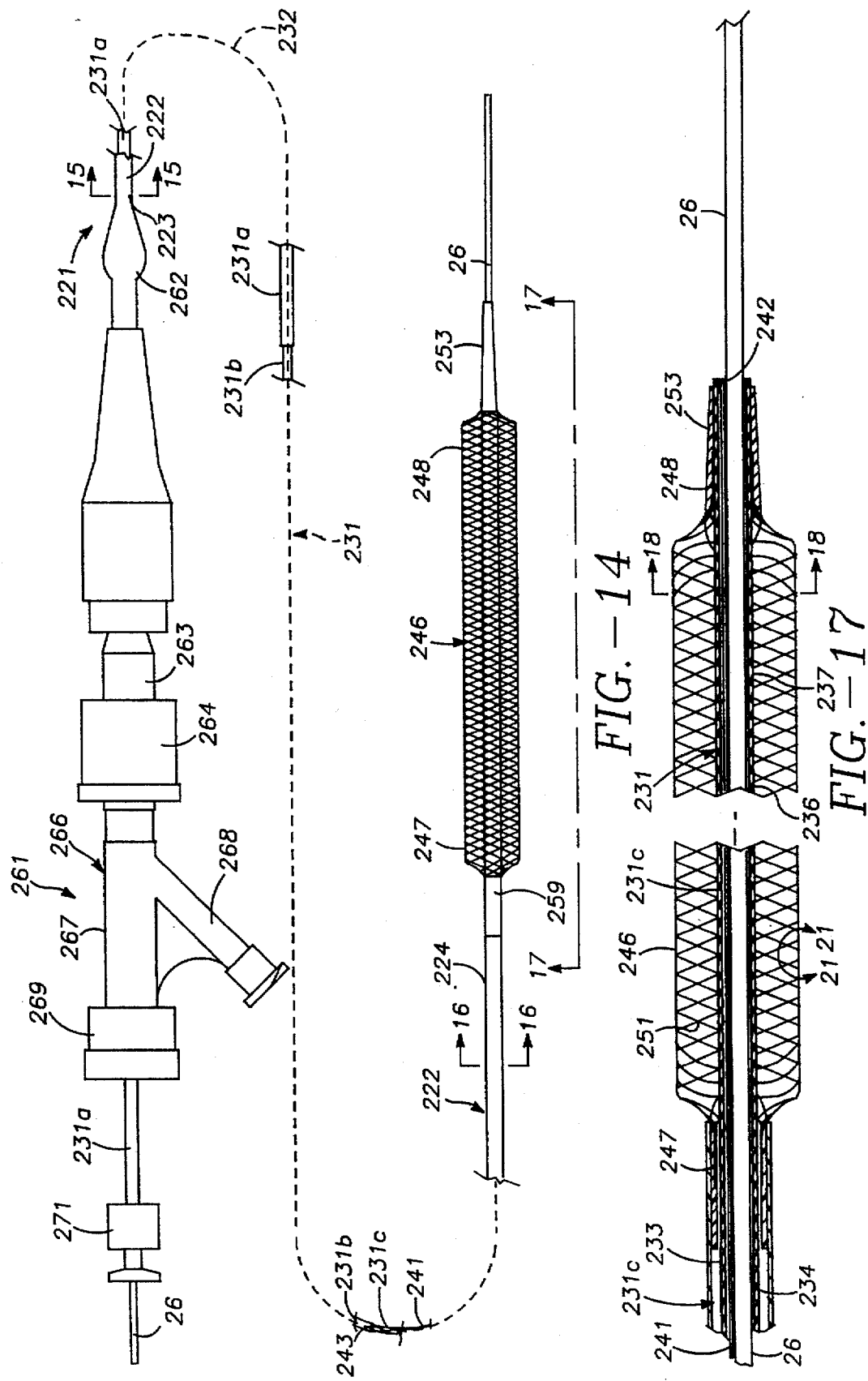

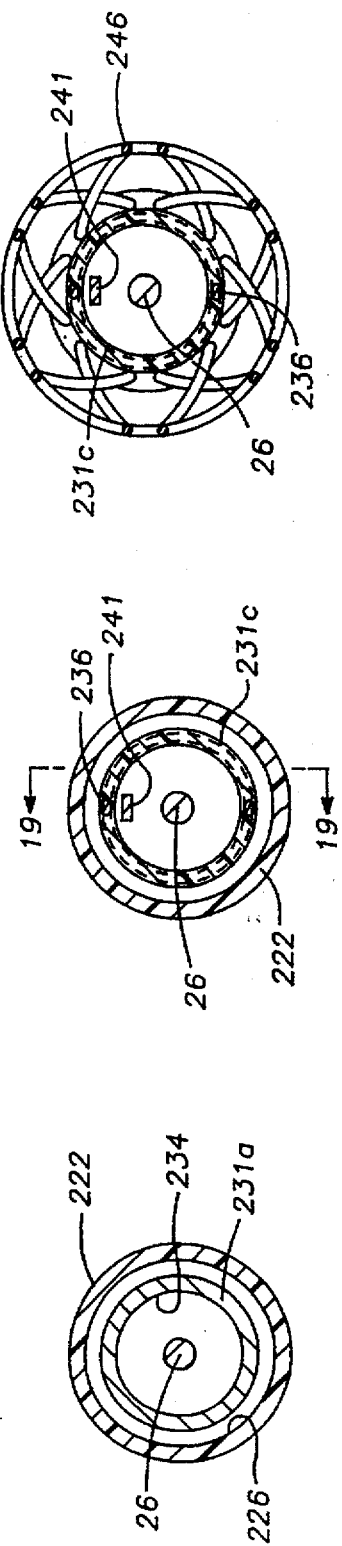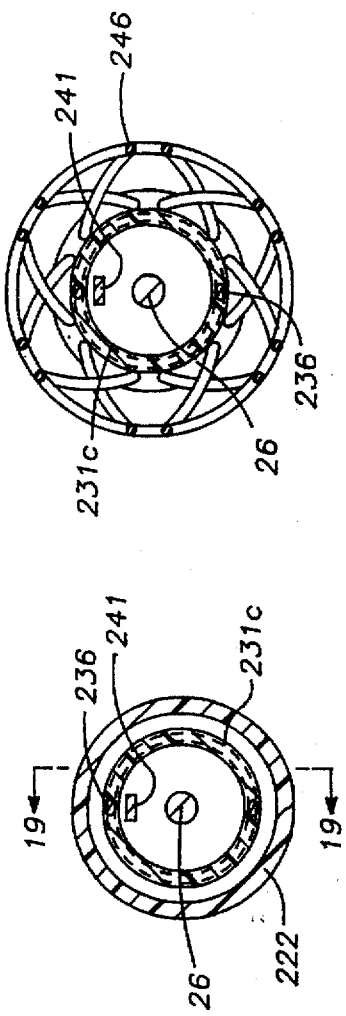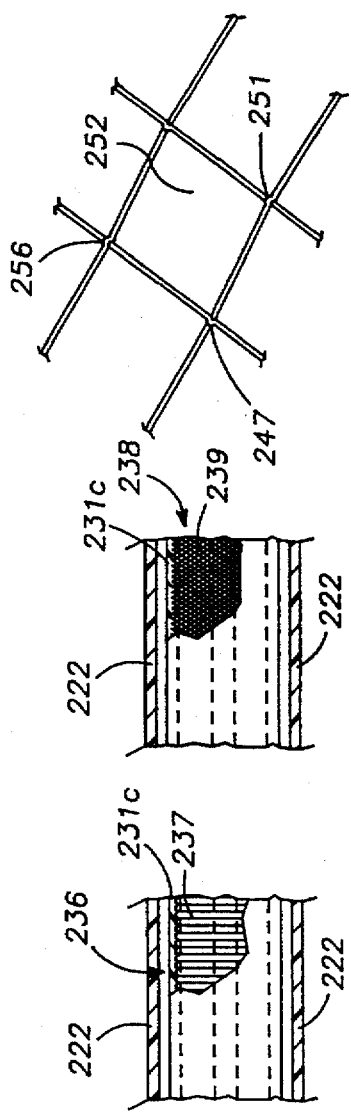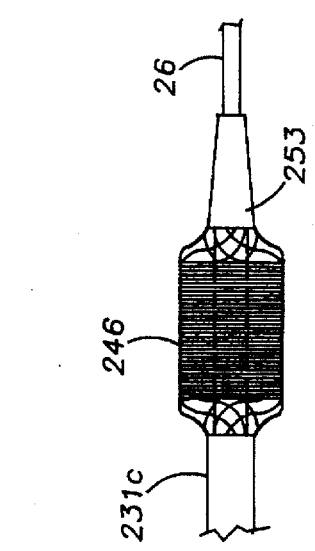

VASCULAR DILATATION DEVICE AND METHOD

This is a continuation-in-part of application Ser. No. 08/353,558 filed Dec. 9, 1994, now U.S. Pat. No. 5,527,282.

This invention relates to a dilatation device and method utilized to enlarge an obstruction in a vessel, a heart valve or other tubular viscera and particularly to a stenosis in a vessel carrying flowing blood and in which it is desired to maintain the flow of blood.

Heretofore balloon catheters and other devices have been utilized for dilating stenoses in blood vessels. In U.S. Pat. No. 5,034,001 a perfusion catheter is disclosed which is used solely for repairing a vessel that has been damaged in an angioplasty procedure. The catheter carries an expandable cage of spirally-arranged wires and a control wire for varying the radial expansion of the cage. The expandable cage is used to press a flap which may be obstructing blood flow against the arterial wall to maintain the potency of the artery. During the period of cage expansion, blood flows through the open weave structure of the cage so that ischemia does not occur distal of the catheter. The expandable cage disclosed does not provide a construction in which sufficient radial forces can be provided to perform an angioplasty procedure. Therefore, it can be seen that there is need for a new and improved vascular dilatation device and method which overcomes these disadvantages.

In general, it is an object of the present invention to provide a vascular dilatation device and method which makes it possible to generate sufficient radial force to compress the stenosis against a vessel wall while allowing free blood flow through the vessel and into side branches from the vessel.

Another object of the invention is to provide a device and method of the above character which can be utilized to dilate a vessel for prolonged periods of time while allowing a perfusion of blood into the vessel distal of the device and into branches from the vessel.

Another object of the invention is to provide a device and method for vascular dilatation which can conform to the linear curvature of a vessel while still providing sufficient radial force to compress the stenosis against the vessel wall.

Another object of the invention is to provide a device and method of the above character in which an elongate hypotube has been provided in the device to enhance pushability and torquability.

Another object of the invention is to provide a device and method of the above character in which an inner tubular member has been provided to enhance the pushability of the dilatation member of the device.

Another object of the invention is to provide a device and method of the above character in which a safety ribbon has been provided within the inner tubular member to prevent undue elongation of the inner tubular member.

Another object of the invention is to provide a device and method of the above character in which a drug can be provided directly to the region of the vessel undergoing dilatation.

Another object of the invention is to provide a device and method of the above character which lends itself to the use of radiocontrast liquids flowing through the device to establish whether or not adequate blood flow is occurring through the device during expansion of the device.

Another object of the invention is to provide a device and method of the above character which permits a rapid exchange system allowing the dilatation catheter to be advanced and withdrawn on a guide wire already in place across the vessel stenosis without the need for long guide wires or extension wires.

Another object of the invention is to provide a device and method of the above character in which a retractable sheath is utilized to facilitate passage of the device through a blood vessel and through a stenosis in the blood vessel without damaging the wall of the vessel.

Another object of the invention is to provide a vascular dilatation device and method of the above character in which an expandable member is provided for dilating a stenosis and which thereafter can be delivered and left in place as a mechanical expanding, self-expanding or balloon expandable stent.

Additional objects and features of the invention will appear from the following description in which preferred embodiments are set forth in detail in conjunction with the accompanying drawings.

FIG. 1 is a side-elevational view partially in section of a vascular dilatation device incorporating the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a cross-sectional view taken along the line 5—5 of FIG. 1.

FIG. 6 is a cross-sectional view taken along the line 6—6 of FIG. 1.

FIG. 7 is a greatly enlarged view of a portion of the dilatation device in the expanded state.

FIG. 8 is a partial side-elevational view of another embodiment of a vascular dilatation device incorporating the present invention with a part of the device covered by a protective material to prevent damage to the vessel wall.

FIG. 9 is a partial side-elevational view of another embodiment of a vascular dilatation device incorporating the present invention which can be utilized in conjunction with a rapid exchange technique.

FIG. 10 is a side-elevational view partially in section of another embodiment of a vascular dilatation device incorporating the present invention which incorporates a retractable sleeve.

FIG. 11 is a side-elevational view of another embodiment of a vascular dilatation device incorporating the present invention in which the device can be utilized as a placement device for the dilatation member so that it can be left in place to serve as a stent.

FIG. 12 is a partial bottom elevation view looking along the line 12—12 of FIG. 11.

FIG. 13 is a cross-sectional view taken along the line 13—13 of FIG. 11.

FIG. 14 is a side-elevational view partially in section of a vascular dilatation device incorporating another embodiment of the present invention.

FIG. 15 is an enlarged cross-sectional view taken along the line 15—15 of FIG. 14.

FIG. 16 is an enlarged cross-sectional view taken along the line 16—16 of FIG. 14.

FIG. 17 is an enlarged side-elevational view of a portion of the device shown in FIG. 14 looking along the line 17—17.

FIG. 18 is a cross-sectional view taken along the line 18—18 of FIG. 17.

FIG. 19 is a cross-sectional view taken along the line 19—19 of FIG. 16.

FIG. 20 is a cross-sectional view similar to FIG. 19 but showing the use of a braid rather than a coil spring.

FIG. 21 is a greatly enlarged fragmentary view taken along the line 19—19 of FIG. 17.

FIG. 22 is a side-elevational view of the distal extremity of the device shown in FIGS. 14–18 showing the distal extremity with the dilatation member in an expanded condition.

In general, the vascular dilatation device of the present invention is used for enlarging an obstruction in a vessel carrying flowing blood. It is comprised of a flexible cylindrical dilatation member adapted to be disposed in the obstruction which has first and second ends and an intermediate portion between the first and second ends. The flexible cylindrical dilatation member also has a flow passage extending therethrough with a diameter and a longitudinal central axis. The diameter of the flow passage is a variable with movement of the first and second ends relative to each other along the longitudinal central axis from a diametrically contracted position to a diametrically expanded condition. The flexible cylindrical dilatation member is comprised of a plurality of flexible elongate elements each of which extends helically about the longitudinal extending central axis. A plurality of the flexible elongate elements having a first common direction of rotation are axially displaced relative to each other and cross a further plurality of the flexible elongate elements also axially displaced relative to each other but having a second common direction opposite to that of the first direction of rotation to form a braided flexible cylindrical member. The crossing of the flexible elongate elements occurs in an area of contact between the flexible elongate elements. First and second means is provided respectively engaging the first and second ends of said flexible cylindrical member for retaining said first and second ends in contracted positions. Means is provided for causing relative axial movement of the first and second ends towards each other to cause the intermediate cylindrical portion of the cylindrical member to contact longitudinally and to expand diametrically by causing the flexible elongate elements in the intermediate portion of the cylindrical member to move closer to each other expanding the diametric dimensions of the cylindrical member and enlarging the obstruction in the vessel or organ. Flexible elongate elements at the first and second ends of the cylindrical member remain contracted around and within first and second means and are thereby prevented from moving closer which maintains spacing between the flexible elongate members so that blood in the vessel can continue to flow through the first and second ends and through the flow passage in the flexible cylindrical member while the cylindrical member is in engagement with the obstruction in the vessel.

More in particular as shown in FIGS. 1–6 of the drawings, the vascular dilatation device 11 shown therein consists of a first or outer flexible elongate tubular member 12 having proximal and distal extremities 13 and 14 with the flow passage 16 extending from the proximal extremity 13 to the distal extremity 14. A second or inner flexible tubular member 21 is coaxially and slidably disposed within the flow passage 16 of the first or outer flexible elongate tubular member 12 and is provided with proximal and distal extremities 22 and 23 with a flow passage 24 extending from the proximal extremity 22 to the distal extremity 23.

A guide wire 26 of a conventional type is adapted to be introduced through the flow passage 24 in the inner flexible elongate tubular member for use in guiding the vascular dilatation device 11 as hereinafter described. The guide wire 26 can be of a suitable size as for example 0.010"–0.018" and can have a suitable length ranging from 150 to 300 centimeters. For example, the first or outer flexible elongate tubular member 12 can have an outside diameter of 1–3 millimeters with a wall thickness of 0.25 millimeters to provide a flow passage of 1.8 millimeters in diameter. Similarly, the second or inner flexible elongate tubular member 21 can have a suitable outside diameter as for example 1.6 millimeters with a wall thickness of 0.25 millimeters and a flow passage 24 of 1.1 millimeters in diameter. The flexible elongate tubular members 12 and 21 can be formed of a suitable plastic as for example a polyimide, polyethylene or Nylon.

In accordance with the present invention a flexible cylindrical dilatation member 31 is provided which has a first or proximal end 32 and a second or distal end 33 with a central or inner flow passage 34 extending from the proximal end 32 to the distal end 33 along a longitudinally extending central axis and has a diameter which is a variable as hereinafter described. The flexible cylindrical dilatation member 31 is comprised of a plurality of flexible elongate elements or filaments 36 each of which extends helically about the longitudinally extending central axis. The flexible elongate elements 36 are formed of a suitable material which can be utilized in the human blood as for example stainless steel, Nitinol, Elgiloy™ or certain other plastic fibers. The flexible elongate elements 36 can have a suitable diameter as for example 0.06–0.20 millimeters or can be configured as a flat wire ribbon. A plurality of the flexible elongate elements 36 have a first common direction of rotation about the central axis as shown in FIGS. 1 and 7 and are axially displaced relative to each other and cross a further plurality of the flexible elongate elements 36 also axially displaced relative to each other but having a second common direction of rotation opposite to that of the first direction of rotation to form a double helix or braided or mesh-like flexible cylindrical member with the crossing of flexible elongate elements 36 occurring in the area of contact between the flexible elongate elements to form openings or interstices 37 therebetween. Thus the flexible elongate elements 36 form a flexible cylindrical dilatation member 31 which provides a central or inner flow passage 34 which is variable in diameter upon movement of the first and second ends of the flexible cylindrical dilatation member 31 relative to each other along the longitudinally extending central axis.

Means is provided for constraining the first and second or proximal and distal ends 32 and 33 of the flexible cylindrical dilatation member 31 and consists of a first or proximal collar 41 and a second or distal collar 42. The first and second collars 41 and 42 are formed of a suitable material such as a polyimide. The first or proximal collar 41 has a suitable length as for example ½" and is sized so that it can fit over the first or proximal end 32 of the flexible cylindrical dilatation member 31 when it is in a contracted position and over the distal extremity 14 of the first or outer flexible elongate member 12. In order to ensure that elongate elements or filaments 36 of the first or proximal extremity 32 are firmly secured to the distal extremity 14 of the first or outer flexible elongate member 12, an adhesive can be provided bonding the first or proximal end 32 to the collar 41 and to the distal extremity 14 of the first or outer flexible elongate tubular member 12. The second or distal collar 42 can be of a suitable size and typically may be slightly smaller in diameter because it need merely secure the elongate element or filaments 36 of the distal end 33 of the flexible cylindrical dilatation member 31 to the distal extremity 23 of the second or inner flexible elongate tubular member 21. An adhesive (not shown) is provided to firmly secure the second or distal end 33 of the flexible cylindrical dilatation member 31 between the second or distal collar 42 and the distal extremity of the inner flexible elongate tubular member 21. In this manner it can be seen that the flexible elongate cylindrical dilatation member 31 has its proximal end curved conically inward toward and secured to the distal extremity of the outer flexible elongate tubular member 12 and the second or distal end 33 of the flexible cylindrical dilatation member 31 also curves conically inward toward and is secured to the distal extremity of the second or inner flexible elongate tubular member 21.

Typically the distance between the first and second collars 41 and 42 can range from between 5 to 150 millimeters. Typically the distal end 23 of the second or inner flexible elongate tubular member 21 extends approximately 30 millimeters beyond the distal extremity 14 of the first or outer flexible elongate tubular member 12.

It can be seen that by moving the first or outer flexible elongate tubular member 12 and the second inner flexible elongate tubular member 21 axially with respect to each other, the first and second ends of the flexible cylindrical dilatation member 31 are moved towards each other causing the elongate elements or filaments 36 of an intermediate portion of the cylindrical dilatation member between the first and second ends to move closer to each other to cause these flexible elongate elements to move into apposition with each other and to expand radially the intermediate portion of the cylindrical dilatation member 31 and to cause the diameter of the central flow passage 34 to increase. The portions of the flexible cylindrical dilatation member 31 immediately adjacent the first and second collars 41 and 42 remain restrained by the collars 41 and 42 causing the flexible elongate elements 36 immediately adjacent to the collars 41 and 42 to curve conically toward and remain crossed and unable to come into close apposition and thereby provide openings or interstices 37 therebetween which remain relatively constant in shape and size so that blood can flow from the first and second ends 32 and 33 through the central or inner flow passage 34 as hereinafter described.

Means is provided in the vascular dilatation device 11 for causing relative movement between the first or outer flexible elongate tubular member 12 and the second or inner flexible elongate tubular member 21 and consists of a screw mechanism 46. The screw mechanism 46 includes a Y-adapter 49 which is provided with a central arm 51 having a lumen 52 through which the second or inner flexible elongate tubular member 21 extends. The lumen or flow passage 52 is in communication with the lumen 16 of outer flexible elongate tubular member 12 and with a flow passage 53 in a side arm 54 which is adapted to receive a syringe (not shown) so that a radiocontrast liquid or a drug can be introduced through the side arm 54 and into the flow passage 52 in the Y-adapter 49 and thence into lumen 16 of outer member 12. The distal end of screw mechanism 46 is provided with a fitting 56 with inner lumen 57 (see FIG. 6) into which the proximal end 13 of flexible elongate tubular member 12 is seated and held in place by an adhesive 58 at the distal end of fitting 56. Lumen 57 is thereby in communication with flow passage 52 of central arm 51 and with flow passage 53 of side arm 54. An O-ring 59 which is adapted to form a fluid-tight seal with respect to the second or inner flexible tubular member 21 is disposed in the lumen 52 of the central arm 51. An interiorly threaded knurled knob 66 is threaded onto an exteriorly threaded member 67 which is secured to and surrounds the proximal extremity 22 of inner flexible elongate tubular member 21. The knob 66 is provided with an inwardly extending flange 68 which seats in an annular recess 69 in the central arm 51. Thus, rotation of the knob 66 causes advancement or retraction of threaded member 67 and the second or inner flexible elongate tubular member 21 with respect to the fitting 56. Indicia 68 in the form of longitudinally spaced-apart rings 70 are provided on the member 67 and serve to indicate the distance which the second or inner flexible elongate tubular member 21 has been advanced and retracted with respect to the first or outer flexible elongate member 12.

A Luer-type fitting 71 is mounted on the proximal extremity 22 of the inner elongate flexible tubular member 21 and is adapted to be engaged by a finger of the hand. The guide wire 26 extends through the fitting 71 and into the lumen 24 of inner elongate flexible tubular member 21.

It should be appreciated that even though one particular screw mechanism 46 has been provided for advancing and retracting the flexible elongate members 12 and 21 with respect to each other, other mechanisms also can be utilized if desired to provide such relative movement.

In order to provide the desired radiopacity for the distal extremity of the vascular dilatation device 11 so that it can be observed fluoroscopically during a dilatation procedure, the collars 41 and 42 can be formed of a radiopaque material as for example by filling the plastic with radiopaque particles of a suitable material such as barium or by providing collars containing radiopaque metals, such as tungsten or platinum or a tungsten platinum alloy. Although the flexible elongate elements 36 which comprise the flexible cylindrical dilatation member 31 have some radiopacity by being formed of a stainless steel or other suitable material such as Elgiloy, there normally is insufficient radiopacity for most medical procedures. Therefore to augment the radiopacity of the flexible cylindrical dilatation member 31, radiopaque wire of a suitable material such as platinum can be wound along with the flexible elongate element 36 to provide the necessary radiopacity. This often may be desirable because this would make it possible to ascertain the position of the flexible cylindrical member and its diameter as it is expanded and retracted between a minimum contracted position and a maximum expanded position by relative movement between the distal extremities of the first or outer flexible elongate member 12 and the second or inner flexible elongate tubular member 21. The use of the helical wraps of platinum does not significantly interfere with the general mechanical properties of the flexible cylindrical dilatation member 31 desired in connection with the present invention. Alternatively, the flexible elongate elements 36 may be plated with a radiopaque metal such as platinum or gold to enhance their radiopacity. Alternatively, the flexible elongate elements may be comprised of hollow wires, the central core of which may be filled with radiopaque metals such as tungsten, gold or platinum or with compound salts of high radiopacity.

Operation and use of the vascular dilatation device 11 may now be briefly described as follows. Let it be assumed that the patient which the medical procedure is to be performed utilizing the vascular dilatation device 11 has one or more stenoses which at least partially occlude one or more arterial vessels supplying blood to the heart and that it is desired to enlarge the flow passages through these stenoses. Typically the vascular dilatation device 11 would be supplied by the manufacturer with the flexible cylindrical dilatation member 31 in its most contracted position to provide the lowest possible configuration in terms of diameter and so that the diameter approximates the diameter of the outer flexible elongate tubular member 12. Thus, preferably, it should have a diameter which is only slightly greater than the tubular member 12, as for example by 1.0–2.3 millimeters. The first and second collars 41 and 42 also have been sized so they only have a diameter which is slightly greater than the outer diameter of the outer flexible elongate tubular member 12. To bring the flexible cylindrical dilatation member 31 to its lowest configuration, the screw mechanism 46 has been adjusted so that there is a maximum spacing between the distal extremity 23 of the inner flexible elongate tubular member 21 and the distal extremity 14 of the outer flexible elongate tubular member 12. In this position of the flexible cylindrical dilatation member 31, the flexible elongate elements 36 cross each other at nearly right angles so that the interstices or openings 37 therebetween are substantially square.

With the screw mechanism 46 in this position, the vascular dilatation device 11 is inserted into a guiding catheter (not shown) typically used in such a procedure and introduced into the femoral artery and having its distal extremity in engagement with the ostium of the coronary artery. Thereafter, the guide wire 26 can be inserted independently of the vascular dilatation device 11. If desired the guide wire 26 can be inserted along with the vascular dilatation device 11 with its distal extremity extending beyond the distal extremity of the vascular dilatation device 11. The guide wire 26 is then advanced in a conventional manner by the physician undertaking the procedure and is advanced into the vessel containing a stenosis. The progress of the distal extremity of the guide wire 26 is observed fluoroscopically and is advanced until its distal extremity extends distally of the stenosis. With the flexible cylindrical dilatation member 31 in its diametrically contracted position, the vascular dilatation device 11 is advanced over the guide wire 26. The distal extremity 23 of the second or inner flexible elongate tubular member 21 is advanced through the stenosis over the guide wire 26 until it is distal to the stenosis and so that the distal extremity 14 of the first or outer flexible elongate tubular member 12 is just proximal of the stenosis.

After the flexible cylindrical dilatation member 31 is in a desired position in the stenosis, the flexible cylindrical dilatation member 31 is expanded from its diametrically contracted position to an expanded position by moving the distal extremities 14 and 23 closer to each other by operation of the screw mechanism 46. This can be accomplished by holding one distal extremity stationary and moving the other distal extremity towards it or by moving both distal extremities closer to each other simultaneously. This movement of the distal extremities 14 and 23 causes collars 41 and 42 to move closer to each other and to cause the central flexible elongate elements 36 forming the double helix mesh of the intermediate portion 31a of the flexible cylindrical dilatation member 31 to move relative to each other to progressively decrease the vertical crossing angle of the double helically wound flexible elongate elements 36 from approximately 160° to 180° in its extended state to 5° to 20° in its axially contracted state and to progressively change the interstices or openings 37 from diamond-shaped openings with long axes parallel to the central longitudinal axis of the catheter in its extended state to substantially square-shaped openings in its intermediately contracted state to elongate diamond-shaped interstices or openings with the longitudinal axes extending in directions perpendicular to the central longitudinal axis with the flexible elongate elements 36 coming into close apposition to each other while at the same time causing radial expansion of the flexible cylindrical dilatation member and to progressively increase the diameter of the central flow passage 34. The expansion of the flexible cylindrical dilatation member 31 in addition to being viewed fluoroscopically can also be ascertained by the indicia 68 carried by the threaded member 67.

During the time that the flexible cylindrical dilatation member 31 is being expanded, it exerts large radial forces against the stenosis to compress the stenosis against the wall of the vessel to dilate or enlarge the stenosis so that an increased amount of blood can flow through the stenosis. The intermediate portion 31a of the flexible cylindrical dilatation member 31 when fully expanded is almost a solid tubular mass which has significant radial strength to make possible compression of the stenosis against the vessel wall. In addition, because of spring-like properties of the expanded flexible cylindrical dilatation member being comprised of helically wound flexible elongate elements 36, the flexible cylindrical dilatation member 31 can conform to a curve within the blood vessel while still exerting significant radial force to the vessel and to make possible compression of the stenosis without tending to straighten the curve in the vessel which typically occurs with standard straight angioplasty balloon systems. Since the ends of the flexible cylindrical dilatation member 31 are constrained by the proximal and distal collars 41 and 42 the flexible elongate elements 36 forming the braided mesh of the flexible cylindrical dilatation member 31 adjacent the distal extremity 23 of the inner elongate flexible tubular member 21 and the distal extremity 14 of the outer flexible elongate tubular member 12 under the collars 41 and 42, respectively, are held in substantially constant angular relationship to each other with the vertical crossing angles between 60° and 180° and are unable to come into close apposition with each other. Therefore the interstices or openings 37 adjacent the collars 41 and 42 remain open because the flexible elongate elements 36 are unable to change from their relatively fixed crossed positions. Blood continues to flow through the central or inner flow passage 34 by passing through the openings 37 in the first or proximal end 32 into the central or inner passage 34 and out the openings in the second or distal end 33. Thus, blood flow through the vessel is not impeded by the expansion of the flexible cylindrical dilatation member 31. It is believed that the flow through the central or inner flow passage 34 can be as great as approximately 10–100 times than that which can be provided with a standard perfusion balloon.

Since blood flows continuously throughout the dilatation procedure, there is no danger of ischemia occurring. This makes it possible to maintain dilatation over extended periods of time when desired. Long dilatations extending over periods of time as for example 30–60 minutes may be utilized if desired. This has an advantage in that in the event a flap or dissection is created during the procedure, sufficient time can be permitted to pass to create an adhesion of a flap in the stenosis to the wall of the vessel thereby preventing further dissection and also eliminating the need for emergency surgery. The additional dilatation time is also believed to be advantageous in decreased recoil of the stenosis in the vessel after the flexible cylindrical dilatation member 31 has been removed resulting in improved dilation and increased luminal diameter after the procedure. It is also believed that prolonged dilatation causes decreased cell growth in the regions where dilatation has taken place which may result in a lower rate of restenosis. In addition dilatation with the vascular dilatation device 11 on the present invention is particularly advantageous in use with patients which have obstructions of a critical nature that cannot even tolerate relatively short periods of dilatation with a balloon without leading to ischemia creating permanent damage or shock to the patient.

The open construction of the flexible cylindrical dilatation member 31 also serves to prevent blocking off of other vessels branching off from the vessel in the region in which dilatation procedures are being performed because the blood can flow through the central interstices 38 of the flexible cylindrical dilatation member 31.

After the dilatation has been carried out for an appropriate length of time, the flexible cylindrical dilatation member 31 can be moved from its expanded position to a contracted position by operation of the screw mechanism 46 in a reverse direction to cause separation of the distal extremities 14 and 23 to thereby cause elongation of the flexible cylindrical dilatation member 31 with a concurrent reduction in diameter.

After the flexible cylindrical dilatation member 31 has been reduced to its contracted or minimum diameter, the vascular dilatation device 11 can be removed along with the guide wire 26 after which the guiding catheter (not shown) can be removed and the puncture site leading to the femoral artery closed in a conventional manner.

Although, the procedure hereinbefore described was for treatment of a single stenosis, it should be appreciated that if desired during the same time that the vascular dilatation advice 11 is within the guiding catheter, other vessels of the patient having stenoses therein can be treated in a similar manner merely by retracting the distal extremity of the vascular dilatation device 11 from the stenosis being treated and then advancing it into another stenosis in another vessel in a similar manner.

Another embodiment of a vascular dilatation device of the present invention is shown in FIG. 8 in which the vascular dilatation device 81 is very similar to the vascular dilatation device 11 with the exception that the flexible cylindrical dilatation member 86 is constructed in a different manner. As shown in FIG. 8, the flexible stainless steel flexible cylindrical dilatation member 86 is formed of flexible elongate elements 36 in the manner hereinbefore described to provide a mesh construction having proximal and distal extremities 87 and 88 and having an intermediate portion 86a between the proximal and distal extremities 87 and 88 and a central flow passage 89 extending therethrough. The flexible cylindrical dilatation member 86 differs from the flexible cylindrical dilatation member 31 in that the outer surface of the intermediate portion 86a between the proximal and distal ends 87 and 88 carries and is covered with a radially expandable and contractible material 91 such as a latex, a silicone or a polymeric plastic tube. Such a flexible, expandable and contractible coating can be readily provided on the flexible cylindrical member 86 such as by placing the same on a mandrel (not shown) and masking off the proximal and distal extremities 87 and 88 by a suitable masking material and then dipping the flexible cylindrical dilatation member into the desired coating material and then cured in an appropriate manner to bond the expandable-contractible material 91 to the flexible elongate elements 36. The coating material 91 applied covers the flexible elongate elements 36 and fills in the interstices or openings 38 between the elements in the intermediate portion 86a. Alternatively, a tubular sleeve of the appropriate dimensions may be made from the latex silicone or polymer material and then placed over the intermediate portion 86a of the flexible cylindrical dilatation member 86 to leave the proximal and distal extremities 87 and 88 exposed. These proximal and distal extremities 87 and 88 can be secured to the distal extremities 14 and 23 by the collars of 41 and 42 in a manner similar that hereinbefore described.

A vascular dilatation device 81 constructed in this manner can be used in the same manner as the vascular dilatation device 11 and can be operated in the same manner. The coated intermediate portion 86a serves to protect the vessel wall from damage and prevents entrapment of tissue between the flexible elongate elements 36 as they are being compressed axially while still permitting the relative free passage of blood into proximal extremity 87 and into the central flow passage 89 and out distal extremity 89.

In connection with the present invention and particularly with the vascular dilatation device 11 in which the intermediate portion 31a still has small interstices between the same, the device 11 can be utilized for prolonged drug infusion while the flexible cylindrical dilatation member 31 remains in its expanded state. The drug may be infused through the side arm 54 which is in communication with the flow passage 16 in the outer flexible elongate tubular member 12. Since the outer flexible elongate tubular member 12 terminates at the distal extremity 14 or at the first or proximal collar 41, a drug infused into the side arm lumen 53 will exit at the proximal extremity of the flexible cylindrical dilatation member 31 and also out of the small interstices 38 provided between the flexible elongate elements 36 in the intermediate portion 31a and directly into the vessel wall at the site of vessel dilatation. Thus drug delivery occurs at the site of the angioplasty procedure in a higher concentration than that which may be tolerated by systemic administration of the drug. Drugs which may be delivered with the device 11 include agents to prevent clotting of the blood, such as heparin, TPA, hirudin or various anti-thrombin agents. Alternatively drugs to prevent cell proliferation and restenosis such as angiopeptin or steroids may be administrated by prolonged infusion during the time that the flexible cylindrical dilatation member is in an expanded condition.

During the time that the flexible cylindrical dilatation member 31 is an expanded position, a radiocontrast liquid may be introduced through the side arm 54 which will pass through the flow passage 16 of the outer flexible elongate tubular member 12 into the proximal extremity of the flexible cylindrical dilatation member 31 through the central flow passage 34 and out the distal extremity 33 through the openings 37 therein. The radiocontrast liquid can then be visualized to ascertain flow through the vessel distal of the lesion in which the dilation is taking place. This also makes it possible to assure that the desired blood perfusion is actually taking place during the dilatation procedure.

Another embodiment of a vascular dilatation device incorporating the present invention is shown in FIG. 9. As shown therein, the vascular dilatation device 101 is constructed in a manner similar to the vascular dilatation device 11 with the exception that it is provided with rapid exchange capabilities. This is accomplished by providing an outer flexible elongate tubular member 102 having a lumen 103 therein and an inner flexible elongate tubular member 106 having a lumen 107 which have the flexible cylindrical dilatation member 31 secured thereto by the proximal and distal collars 41 and 42. The outer flexible elongate tubular member 102 is provided with a port or opening 111 into the corresponding lumen 103 and which is 13–60 centimeters from the distal extremity 32 of the flexible cylindrical dilatation member 31. A corresponding port or opening 112 into corresponding lumen 107 is provided within the inner flexible elongate tubular member 106. These ports 111 and 112 are positioned so that when the flexible cylindrical dilatation member 31 is in its expanded position with the distal extremities of the members 102 and 106 being in closest proximity to each other, the openings 111 and 112 are in registration with each other. In this position, the vascular dilatation device 111 can be loaded onto the guide wire 16 by advancing the most proximal extremity of guide wire 26 first into lumen 107 of the distal extremity of the inner flexible elongate member 106 and then back through port or opening 112 and port 111 which are in registration and out of the flexible elongate tubular member 102. The flexible cylindrical dilatation member 31 is next contracted from its diametrically expanded condition to a contracted condition by moving the distal extremities of outer and inner flexible elongate tubular members 102 and 106 further apart by operation of screw mechanism 46. This procedure is performed while maintaining a stable position of the external position of guide wire 26 in a constant position in relation to port 111. As the distal extremity of flexible tubular member 106 is moved further from the distal extremity of flexible elongate tubular member 102, port 112 will move out of registration with port 111 while maintaining guide wire 26 within lumen 107 and advancing the distal extremity of the flexible elongate tubular member 106 along the guide wire 26. In this diametrically contracted state of the flexible cylindrical dilatation member 31, vascular dilatation device 101 may be advanced along guide wire 26 through the region of stenosis in the blood vessel and expansion of flexible cylindrical dilatation member 31 may occur using screw mechanism 46 in the manner previously described. Once vascular dilatation has been completed, flexible cylindrical dilatation member 31 can be diametrically contracted and the vascular dilatation device 101 may be removed from the blood vessel and the guiding catheter by maintaining a stable position of guide wire 26 in relation to the blood vessel and retracting device 101 along guide wire 26 until the distal extremity of inner flexible member 106 exits the patient's body. The vascular dilatation device 101 may now be rapidly exchanged with another vascular dilatation device 101 as for example one having a flexible cylindrical dilatation member 31 which can be increased to a larger diameter over a standard 150 centimeter length guide wire 26.

Still another vascular dilatation device 121 incorporating the present invention is shown in FIG. 10 which is very similar to the vascular dilatation device 11 hereinbefore described with the exception that it is provided with a retractable sheath 126 which extends the entire length of the outer flexible elongate tubular member 12 and extends over the flexible cylindrical dilatation member 31 to facilitate passage of the flexible cylindrical dilatation member 31 into and through a blood vessel without damage to the blood vessel by the exposed flexible elongate elements 36 of the flexible cylindrical dilatation member 31. The retractable sheath 126 extends proximally and extends through the screw mechanism 46 and is provided with a hook-like member 131 which is slidably mounted in a slot 132 located along central arm 132a of screw adapter 49a. The hook-like member 131 can travel through a distance permitting retraction of the retractable sheath 126 from over the flexible cylindrical dilatation member 31 so that it can be expanded in the manner hereinbefore described. If desired, the hook-like member 131 can be provided with a portion 131a which extends distally and extends through a hole 137 provided in the knob 66 to prevent rotation of the knob until the hook-like member 131 has been retracted to uncover the flexible cylindrical dilatation member 31. This prevents rotation of the screw mechanism 46 and expansion of the flexible cylindrical dilatation member 31 until the retractable sheath 126 has been fully retracted. Thereafter, the dilatation device 121 can be operated in a manner similar to that hereinbefore described.

Another vascular dilatation device 151 incorporating the present invention is shown in FIGS. 11–13 and consists of a first or outer flexible elongate tubular member 152 which has proximal and distal extremities 153 and 154 with a flow passage 156 extending therebetween. It also consists of a second or inner flexible elongate tubular member 157 which has proximal and distal extremities 158 and 159 with a flow passage 161. There is also provided a third or middle flexible elongate tubular member 162 which has proximal and distal extremities 163 and 164 and a flow passage 166 extending therethrough. The third or middle flexible elongate tubular member 162 is coaxially mounted within the passage 156 of the first or outer flexible elongate tubular member 152 which is slidable thereon. The second or inner flexible elongate tubular member 157 slidably mounted in the flow passage 166 of middle tubular member 162. The guide wire 26 is adapted to extend through the flow passage 161 of the second or inner flexible elongate tubular member 157.

A flexible cylindrical dilatation member 31 of the type hereinbefore described is a part of the vascular dilatation device 151 and has its first or proximal extremity 32 retained by slip friction fit and is disposed in the passageway 156 between the outer surface of the third or middle flexible elongate tubular member 162 and the inner surface of the first or outer flexible elongate tubular member 152 with the distal extremity 154 of the first or outer flexible elongate tubular member 152 terminating just short of the distal extremity 164 of the third or middle flexible elongate tubular member 162. The distal extremity 33 of the flexible cylindrical dilatation member 31 is also frictionally retained between a collar or sleeve 171 mounted on the distal extremity 159 of the second or inner flexible elongate tubular member 158 and retaining the distal extremity 33 in frictional engagement with the distal extremity 159 of the second or inner flexible elongate tubular member 157 to thereby constrain the proximal and distal ends 32 and 33 of the flexible cylindrical dilatation member 31 in the manner hereinbefore described in FIG. 1 with the collars 41 and 42. In order to secure the distal extremity of the collar 171 to the distal extremity 159 of the second or inner flexible elongate tubular member 151, a small band of adhesive 172 is applied between the collar 171 and the distal extremity 159 with care taken to prevent the adhesive from contacting the constrained flexible elongate elements 36 of distal end 33.

A y-adapter 176 forms a part of the vascular dilatation device 151 and is provided on the distal extremity. The y-adapter 176 includes a central arm 177 having a lumen 178 therein and a side and a side arm 179 having a lumen 180 therein. The central arm 177 is provided with a cylindrical knurled knob 181 having internal helical threads 182 formed on the interior surface thereof. The cylindrical knob 181 is provided with an inwardly extending flange 183 which seats in an annular recess 184 in the central arm 177 of the y-adapter 176. The knob 181 threadedly engages exterior helical thread 182 on the proximal extremity of the first or outer elongate tubular member 152. The distal extremity of central arm 177 passes through lumen 156 of the outer elongate tubular member 152 and interior of lumen 166 of the middle elongate tubular member 162 and is adhesively attached to the proximal extremity 163 of middle elongate tubular member 162 such that the lumen 178 of the central arm 177 is in communication with lumen 166 of the third or middle tubular member 162. Adhesive attachment of middle tubular member 162 to central arm 177 prevents axial movement and rotation of tubular member 162 with respect to y-adapter 176 when cylindrical knob 181 is rotated, engaging external threads 182 of the proximal extremity 153 of outer elongate tubular member 152 and causing axial movement of the distal extremity 154 of outer tubular member 162 with respect to distal extremity 164 of middle elongate tubular member 162.

An externally threaded cylindrical member 196 is secured surrounding area intermediate the ends of a guide member 197 and is formed of a suitable material such as stainless steel by suitable means such as an adhesive. The guide member 197 extends through a passage 198 provided in the central arm 177 and is secured to the proximal extremity 158 of the second or inner flexible elongate tubular member 157 by suitable means such as an adhesive. A knurled knob 201 having internal threads threadedly engages the cylindrical member 196 and is mounted in a fixed axial position on the central arm 177 and is rotatable therewith to cause axial movement of the second or inner flexible elongate tubular member 157. An upstanding pin 206 is provided on the guide member 197 and extends radially therefrom through an elongate slot 207 formed in the central arm 177 of the y-adapter 176. The slot 207 is provided with circumferentially spaced apart parallel elongate portions 207a and 207b which are adjoined by an intermediate portion 207c which extends at right angles between the same. Indicia 209 are provided alongside the slot 207 and serve to indicate various positions of the second or inner flexible elongate tubular member 157.

As can be seen and as hereinafter described, the vascular dilatation device 151 is particularly adapted for use in dilatation in the manner hereinbefore described with the previous embodiments but also has the capability when desired to disengage the flexible cylindrical dilatation member 31 so that it can self expand and remain in the dilated stenosis so that it can serve as a permanent stent.

Assuming that the flexible cylindrical dilatation member 31 has its proximal and distal extremities 32 and 33 frictionally engaged as hereinbefore described, the flexible cylindrical dilatation member 31 can be moved to a fully extended position by rotating the knurled knob 201 to cause the distal extremity 159 of the second or inner flexible elongate tubular member 151 to be moved away from the distal extremity 154 of the first or outer flexible elongate tubular member 152 so as to present the lowest possible profile for introduction of the vascular dilatation device into the vasculature of the patient in the manner hereinbefore described. Typically, the guide wire 12 is advanced through the stenosis after which the distal extremity 159 of the second or inner flexible elongate tubular member 157 is advanced through the stenosis until it is distal of the stenosis and with the distal extremity 154 of the first or outer flexible elongate tubular member 152 being proximal of the stenosis. Dilatation can then be carried out by adjustment of the knurled knob 203 by rotating it in an opposite direction to cause the distal extremity 159 to be brought into closer proximity to the distal extremity 154 to cause radial expansion of the flexible cylindrical dilatation member 31 as hereinbefore described and to cause dilation of the stenosis or obstruction in the vessel of the patient. During this dilatation as hereinbefore described, blood can readily flow through the open interstices 37 of the proximal and distal extremities 32 and 33 of the flexible cylindrical dilatation member 31 to prevent ischemia as hereinbefore described.

After the desired dilatation has been accomplished and it is desired to leave the flexible cylindrical dilatation member 31 in the stenosis, it can be released from the vascular dilatation device 351 in the following manner. While holding the vascular dilatation device 151 stationary in the patient's vessel, the knob 201 can be rotated to move the distal extremity 159 of the second or inner flexible elongate tubular member 157 to cause elongation of the flexible cylindrical dilatation member 31. This rotation of knob 203 with distal movement of distal extremity 159 of inner tubular member 157 is accompanied by axial distal movement of upstanding pin 206 provided on guide member 197 through slot portion 207b until the pin approximates slot portion 207c at right angles to slot portion 207b and pin 206 is prevented from any further axial movement. This position of pin 206 at the intersection of slot portions 207b and 207c corresponds to the distance between the distal extremity 159 of inner tubular member 157 and distal extremity 154 of outer tubular member 152 equaling the elongation limit of flexible cylindrical dilatation member 31. Pin 206 may now be manually displaced along slot portion 207c until it aligns with slot portion 207a. Further advancement of pin 206 along slot portion 207a is now possible by rotation of knob 201 and further advancement of guide member 197 and increase in axial distance between the distal extremity 159 of inner tubular member 157 and the distal extremity 154 of outer tubular member 152. Continued rotation of the knob 201 causes the distal extremity 33 of the flexible cylindrical dilatation member 31 to be released from between the collar 171 and the outer surface of the second or inner flexible elongate tubular member 157. Upon release, the distal extremity 33 of the flexible cylindrical dilatation member 31 will self expand and open to an increased diameter. Thereafter, the proximal extremity 32 of the flexible cylindrical dilatation member 31 is released by rotating the cylindrical knob 181 to cause the first or outer flexible elongate tubular member 152 to be retracted with respect to the stationary third or middle flexible elongate tubular member 162. This rotation is continued until the proximal extremity 32 is released permitting it also to self expand so that the flexible cylindrical dilatation member 31 is free within the confines of the stenosis and permitting it to expand to engage the stenosis and to serve as a permanent stent within the stenosis.

The remaining part of the vascular dilatation device 151 can now be removed by retraction of the same. This can be readily accomplished since the distal extremity 33 of the flexible cylindrical dilatation member 31 has expanded, the collar 171 and the distal extremity 159 of the second or inner flexible elongate tubular member 157 can be retracted therethrough. The collar 171 can then pass through the expanded proximal extremity 32 and be retracted along with the middle and outer flexible elongate tubular members 162 and 152 after which the guiding catheter can be removed and the puncture site sutured in an appropriate manner.

Thus it can be seen that the vascular dilatation device 151, in addition to serving as a dilatation device also serves as a stent placement device.

Another embodiment of a vascular dilatation device 221 incorporating the present invention is shown in FIGS. 14–19. As shown therein, the device 221 consists of a flexible elongate tubular member 222 having proximal and distal extremities 223 and 224. The flexible elongate tubular member 222 can be formed out of a suitable material such as a polyethylene or a polyimide.

A lumen 226 extends from the proximal extremity 223 to the distal extremity 224 and has a size which is the same as in the first or outer flexible elongate tubular member 12 hereinbefore described in connection with the previous embodiments. Thus, it can have a suitable size as for example 5-French. A second or inner flexible elongate tubular member 231 is provided which is slidably and coaxially disposed within the lumen 226. It is provided with proximal and distal extremities 232 and 233 with a lumen 234 extending from the proximal extremity 232 to the distal extremity 233. In the present embodiment of the invention, the inner flexible elongate tubular member 231 serves as a support member. The flexible elongate tubular member 231 is formed of three portions 231a, 231b and 231c with the first portion 231a being at the proximal extremity 232 and the second portion 231b extending from the proximal extremity 232 to the near distal extremity 233. The portion 231a is formed of a hypotube having an outside diameter of 0.010" to 0.042" and an inside diameter of 0.012" to 0.030" to provide a wall thickness of 0.002" to 0.010". The portion 231a has a suitable length as for example 10–30 centimeters. The second portion 231b can be formed so that it has an outside diameter of 0.016" to 0.042" and an inside diameter of 0.012" to 0.030" to provide a wall thickness of 0.002" to 0.010". Thus it can be seen that the portion 231a has a greater wall thickness and provides additional stiffness and rigidity. A guide wire 26 of the type hereinbefore described is slidably disposed in the lumen 234. The lumen 234 in the flexible elongate tubular support member 231 is sized so that it can readily accommodate the guide wire 26. Thus, if a guide wire having a size 0.014" is used, the lumen 226 should have a diameter which is greater than 0.016" to 0.018".

The third portion 231c of the flexible elongate tubular support member 231 is formed of a suitable material such as plastic, as for example a polyimide. It has a suitable length, as for example from 20–40 centimeters and preferably a length of approximately 30 centimeters. The portion 231c is bonded to the distal extremity of the portion 231b by suitable means such as an adhesive. In order to increase the pushability of the portion 231c of the flexible elongate tubular member 231 while retaining its flexibility, a coil spring 236 is embedded within the plastic forming the portion 231c. The coil spring 236 is provided with a plurality of turns 237 as shown in detail in FIG. 19, which preferably are immediately adjacent or in apposition to each other to provide for maximum pushability. The coil spring 236 should extend at least throughout the length of the flexible cylindrical dilatation member 241 mounted coaxially thereover as hereinafter described. In addition, as shown the coil spring 236 can extend the entire length of the portion 231c. The coil spring 236 is carried by the portion 231c and preferably can be embedded or encapsulated within plastic 238 of the same type forming the tubular support member 231. Such embedding of the coil spring 236 prevents uncoiling of the coil elements or turns 237 and elongation of the flexible elongate tubular member 231 upon retraction of the inner elongate tubular member 231 into the outer elongate tubular member 226 with decrease in distance between proximal and distal ends of the flexible cylindrical dilatation member 241. Alternatively, as shown in FIG. 20, a braided member 238 may be substituted for the coil spring 236 and also encapsulated or embedded with the plastic forming portion 231c. Such encapsulation also prevents elongation of portion 231c upon retraction of the flexible elongate tubular support member 231 into the outer elongate tubular member 226. The metal braid 238 formed of a suitable material such as stainless steel wires 239 of a suitable diameter ranging from 0.001" to 0.003" can be used to form the mesh for the braided member 238. The braided member 238 increases the pushability of the portion 231c of the inner flexible elongate tubular member 231 and also prevents substantial elongation of the inner flexible elongate tubular member 231.

A safety ribbon 241 is provided within the inner flexible tubular member 231 to prevent elongation of the portion 231c of the inner flexible elongate tubular member 231 and extends from the distal extremity Of portion 231b to the distal extremity of portion 231c. The safety ribbon 241 can be formed of a suitable material such as stainless steel having a diameter area of 0.002" to 0.004". The safety ribbon 241 is disposed adjacent the portion 231c of the flexible elongate tubular member 231, and preferably as shown extends interiorly of the portion 231c in the lumen 234 and has its distal extremity secured to the distal extremity of the portion 231c by solder 242. The safety ribbon 241 has its proximal extremity secured to the distal extremity of the portion 231b of the inner flexible elongate tubular member 231 by the use of solder 243 (see FIG. 14).

A flexible cylindrical dilatation member 246 is provided with proximal and distal extremities 247 and 248 as shown in FIG. 17 and is disposed coaxially on the portion 231 of the inner flexible elongate tubular member 231. The flexible cylindrical dilatation member 246 is constructed in a manner similar to the flexible cylindrical dilatation member 31 hereinbefore described and is provided with a plurality of flexible elongate elements or filaments 251 in which a plurality of elements 251 have a first common direction of rotation about the central axis as shown in FIG. 14 and are axially displaced relative to each other and cross over a further plurality of the flexible elongate elements 251 also axially displaced relative to each other but having a second common direction of rotation opposite to that of the first direction of rotation to form a double helix, braided or mesh-like flexible cylindrical dilatation member 246 with the crossing of the flexible elongate elements 251 occurring in the area of contact between the flexible elongate elements 251 to form openings or interstices 252 therebetween. The solder 242 used for securing the safety ribbon 238 to the coil spring 236 is also used for securing the distal extremity 248 of the cylindrical dilatation member 246 to the distal extremity of the inner flexible elongate tubular member 231. A sleeve 253 of heat shrink tubing covers the solder 242.

In order to increase the radial forces generated by the flexible cylindrical dilatation member 246, it has been found that it is desirable to provide undulations 256 in which there is an undulation 256 present at each cross-over point of the filaments 251. Thus, as shown in FIG. 21, which is a fragmentary view of the cylindrical dilatation member 246 shown in FIG. 17, an undulation 256 is provided in each of the plurality of flexible elongate elements 251 having a first direction of rotation at every other cross-over point with the plurality of flexible elongate elements having a second common direction of rotation about the central axis and wherein the undulations in the adjacent elements 251 are offset by one cross-over point so that in the resulting mesh or braid construction, the undulations 256 in one of the elements 251 having a first direction of rotation overlies every other cross-over point of the element 251 having a second direction of rotation and, conversely, every element 251 having a second direction of rotation has an undulation 256 therein at every other cross-over point of the elements 251 having a first direction of rotation. These undulations 256 can be in the form of obtuse angle bends having straight portions extending from both sides of the bend, or alternatively can be in the form of arcuate portions having a diameter corresponding generally to the diameter of the elements 251. Thus, it can be seen that the undulations 251 make it possible for one of the elements 251 to support the other of the elements at each cross-over point, thereby preventing slippage of the elements 251 with respect to each other and thereby causing greater radial forces to be applied when the flexible cylindrical dilatation member 246 is expanded as hereinafter described.

The flexible cylindrical dilatation member 246 is comprised of 21–64 individual elements 251 formed of 0.020 millimeter diameter wire of a suitable metal such as stainless steel helically wound around a longitudinal central axis. The helices are wound in opposite directions. Stretching or elongation of the flexible cylindrical dilatation member 246 results in a reduction in diameter of the flexible cylindrical dilatation member 246. Mechanical fixation of the proximal and distal extremities 247 and 248 of the flexible cylindrical dilatation member 246 holds these extremities in reduced diameter configurations. The positions of the elements 251 in these extremities cannot change in relation to each other. Therefore, the crossing angles of the elements 251 remain constant. Shortening of the flexible cylindrical dilatation member 246 with the ends fixed results in the formation of a cylindrical center section of great rigidity with the elements 251 in close apposition to each other. The tapered proximal and distal extremities of the flexible cylindrical dilatation member 246 causes the stresses on the individual elements 251 to be balanced. Since the proximal and distal extremities 247 and 248 are held in constant tapered positions, the interstices 252 between the elements 251 are maintained allowing blood to flow into and out of the cylindrical center section when the flexible cylindrical dilatation member 246 is shortened as shown in FIG. 22. Shortening of the flexible cylindrical dilatation member or spring 246 results in a significant increase in the metal density per unit length in the center portion of the flexible cylindrical dilatation member 246 while the metal density at the ends is relatively constant. This increase in metal density in the center section results in significant radial force generation as the elements 251 are compressed in a longitudinal direction into preformed diameters.

Use of the helically wound coil spring 236 or the braid 238 which serves with or as part of the inner elongate tubular member 231 and coaxially disposed within the flexible cylindrical dilatation member 246 provides greatly improved pushability and axial column strength for causing elongation of the cylindrical dilatation member 246 while providing the desired flexibility so that tortuous curves can be negotiated during deployment of the vascular dilatation device 221. The portion 231c of the flexible elongate tubular member 231, and particularly within the flexible cylindrical dilatation member 246, has a relatively small diameter so that it does not adversely affect the stenosis crossing profile for the vascular dilatation device 221. The use of the inner or safety ribbon 241 prevents undue elongation and unwinding of the coil spring 236 forming a part of portion 231c of the flexible elongate tubular member 231 when the flexible cylindrical dilatation member 246 is lengthened or elongated. The pull or safety ribbon 241 also limits elongation of the flexible cylindrical dilatation member 246 and thereby prevents the elements 251 from being broken off or pulled away from the solder joints 253.

The proximal extremity 223 of the outer flexible elongate tubular member 222 of the vascular dilatation device 221 is provided with control means 261 for causing relative movement between the first or outer flexible elongate tubular member 222 and the second or inner flexible elongate tubular member 231 and can be similar to that hereinbefore described. This control means 261 consists of a fitting 262 which is bonded to the proximal extremity 223 of the outer flexible elongate tubular member 222. The fitting 262 is provided with a male Luer fitting 263 removably mated with a female Luer fitting 264 carried by a Y-adapter 266 which is provided with a central arm 267 and a side arm 268. The side arm 268 is in communication with the lumen 226 of the outer flexible elongate tubular member 222. The inner flexible elongate tubular member 231 extends through the central arm 267 of the y-adapter 266. A rotatable knob 269 is provided on the central arm of the y-adapter 266 for forming a fluid-tight seal between the central arm 267 and the portion 231a of the inner flexible elongate tubular member 231. A male Luer fitting 271 is mounted on the proximal extremity of the portion 231a. The guide wire 26 extends through the lumen 234 of the inner flexible elongate tubular member 231 and extends beyond the distal extremity thereof.

As hereinbefore described, the control means 261 can include means such as a screw mechanism for causing relative movement between the outer flexible elongate tubular member 222 and the inner flexible elongate tubular member 231.

Operation and use of the vascular dilatation device 221 is substantially similar to that hereinbefore described with respect to the previous embodiments. The vascular dilatation device 221 however has a member of features which may be more advantageous in certain medical procedures. Thus in medical procedures where improved pushability and torquability is required the use of the metal hypotube for the portion 231b of the flexible elongate tubular member provides additional pushability and torquability for the catheter facilitating advancement of the vascular dilatation device 221 through more difficult stenoses, particularly where additional torquability and pushability are desired. This is also true with the distal extremity of the vascular dilatation device 221 in which the inner flexible elongate tubular member 231 has the distal portion 231c thereof that includes the compressed coil spring 236 or braided member 238 which extends at least through the flexible cylindrical dilatation member 246 to provide additional pushability for the flexible cylindrical dilatation member 246 while still retaining the desired flexibility. Even though improved pushability is provided, the distal extremity of the vascular dilatation device 221 is still very flexible permitting it to track tortuosities in the vessels being negotiated thereby. Also because of the pushability of the inner flexible elongate tubular member 231, it is possible to obtain maximum extension of the flexible cylindrical dilatation member 246 and thereby a minimum diameter to facilitate crossing of a stenosis with very small openings therethrough with the vascular dilatation device 221. The safety ribbon 241 prevents undue elongation of the inner flexible elongate tubular member 231. In addition, encapsulation of the compressed coil spring 236 or braided member 238 also prevents elongation of the inner flexible elongate tubular member 231.

When the flexible cylindrical dilatation member 246 is being expanded by decreasing the length of the same, such as in the manner shown in FIG. 21, the diameter of the flexible cylindrical dilatation member is increased to its maximum size with great rigidity because of the undulations 256 provided in the elements 251 of the flexible cylindrical dilatation member or flexible cylindrical dilatation member 246. These undulations 256 aid providing greater radial forces while still retaining the conical or tapered ends with the open interstices to readily permit blood to pass through the flexible cylindrical dilatation member 246 during the time that the flexible cylindrical dilatation member 246 has been expanded to its maximum diameter to apply maximum radial forces to the stenoses which is being dilated during the procedure.

From the foregoing, it can be seen that there has been provided a vascular dilatation device which can be used in the same manner as a balloon catheter in performing an angioplasty procedure with the outstanding advantage that blood can continue to flow to the distal blood vessel during the dilatation procedure. This permits a longer vessel dilatation without tissue ischemia. Significantly more blood can flow than through a standard perfusion balloon. In addition a perfusion of side branches continues through the flexible cylindrical member. Prolonged drug infusion may also be undertaken with delivery of drug directed directly to the site of the angioplasty procedure.

I claim:

1. A vascular dilatation device for enlarging a flow passage in an obstruction in a vessel carrying flowing blood comprising a flexible cylindrical dilatation member for placement in the flow passage in the obstruction and having first and second ends and an intermediate portion between the first and second ends, said flexible cylindrical dilatation member also having an interior flow passage extending therethrough with a diameter and a longitudinally extending central axis, said diameter of said flow passage being variable with movement of the first and second ends relative to each other along the longitudinally extending central axis from a contracted position to an expanded position, said expanded position permitting blood to flow through the flexible cylindrical dilatation member and means for causing relative axial movement of said first and second ends towards each other from an extended position to a contracted position, said means for causing relative axial movement including an outer flexible elongate tubular member having proximal and distal extremities, said distal extremity of the outer flexible elongate tubular member being secured to the first end of said flexible cylindrical dilatation member and an inner flexible elongate tubular member having proximal and distal extremities and disposed between the first and second ends of the flexible cylindrical dilatation member, said distal extremity of the inner flexible elongate tubular member being secured to the second end of said flexible cylindrical dilatation member, said inner flexible elongate tubular member having sufficient rigidity for causing elongation of the cylindrical dilatation member so as to decrease its diameter and cause advancement of the cylindrical dilatation member through the obstruction in the vessel while preventing axial contraction of the cylindrical dilatation member.

2. A device as in claim 1 further including a coil spring carried by said inner flexible elongate tubular member, said coil spring having turns which are in apposition to each other.

3. A device as in claim 2 wherein said coil spring is embedded in the inner flexible elongate tubular member.

4. A device as in claim 2 further including a safety ribbon secured to the inner flexible elongate tubular member and serving to prevent elongation of the coil spring at the distal extremity of the inner flexible elongate tubular member.

5. A device as in claim 1 further including a braided member embedded in the inner flexible elongate tubular member.

6. A device as in claim 1 wherein said inner flexible elongate tubular member is formed of a plastic.

7. A device as in claim 1 for use with a guide wire wherein said inner flexible elongate tubular member has a lumen extending therethrough, said lumen being sized so that it is adapted to having the guide wire slidably mounted therein.

8. A vascular dilatation device for enlarging a flow passage in an obstruction in a vessel carrying flowing blood comprising a flexible cylindrical dilatation member for placement in the flow passage in the obstruction and having first and second ends and an intermediate portion between the first and second ends, said flexible cylindrical dilatation member also having an interior flow passage extending therethrough with a diameter and a longitudinally extending central axis, said diameter of said flow passage being variable with movement of the first and second ends relative to each other along the longitudinally extending central axis from a contracted position to an expanded position, said expanded position permitting blood to flow through the flexible cylindrical dilatation member and means for causing relative axial movement of said first and second ends of the flexible cylindrical dilatation member towards each other from an extended position to a contracted position, said means for causing relative axial movement including an outer flexible elongate tubular member having proximal and distal extremities, said distal extremity of the outer flexible elongate tubular member being secured to the first end of said flexible cylindrical dilatation member and an inner flexible elongate tubular support member having proximal and distal extremities and disposed between the first and second ends of the flexible cylindrical dilatation member, said distal extremity of the inner flexible elongate tubular support member being secured to the second end of said flexible cylindrical dilatation member, said inner flexible elongate tubular support member extending from the proximal extremity of the outer flexible elongate tubular member to a location at least near the distal extremity of the outer flexible elongate tubular member, said inner flexible elongate tubular support member having sufficient rigidity for causing elongation of the cylindrical dilatation member so as to decrease its diameter and cause advancement of the cylindrical dilatation member through the obstruction in the vessel while preventing axial contraction of the cylindrical dilatation member, said inner flexible elongate tubular support member also providing increased pushability and torquability to the device.

9. A device as in claim 8 wherein said distal extremity of the inner flexible elongate tubular support member is coupled to the second end of the flexible cylindrical dilatation member.

10. A device as in claim 8 further including a coil spring carried by said inner flexible elongate tubular support member, said coil spring having turns which are in apposition to each other.

11. A device as in claim 8 further including a braided member embedded in the inner flexible elongate tubular support member.

12. A vascular dilatation device for enlarging a flow passage in an obstruction in a vessel carrying flowing blood comprising a flexible cylindrical dilatation member for placement in the flow passage in the obstruction and having first and second ends and an intermediate portion between the first and second ends, said flexible cylindrical dilatation member having an interior flow passage extending therethrough with a diameter and a longitudinally extending central axis, said diameter of said flow passage being variable with movement of the first and second ends relative to each other along the longitudinally extending central axis and means for causing relative axial movement of the first and second ends towards each other from an extended position of a decreased diameter to a contracted position of an increased diameter, said means including a relatively rigid flexible elongate tubular support member extending from near the proximal extremity of the outer flexible elongate tubular member to a region in the distal extremity of the outer flexible elongate tubular member, said flexible elongate tubular support member providing increased pushability and torquability to the device.

13. A device as in claim 12 wherein at least a portion of said flexible elongate tubular support member is formed of metal.

14. A device as in claim 12 wherein said flexible cylindrical dilatation member is in the form of a dilatation spring comprised of a plurality of flexible elongate elements extending helically about the longitudinally extending central axis and having first and second common directions of rotation to form a braid with cross-over points, said elements being formed with undulations therein disposed at the cross-over points to inhibit slipping movement of the flexible elements with respect to each other during contraction of the flexible cylindrical dilatation member to increase the radial forces being applied to the obstruction by the flexible cylindrical dilatation member during contraction of the flexible cylindrical dilatation member.

15. A device as in claim 14 wherein the undulations in each of the flexible elongate elements occurs at every other cross-over point.

16. A device as in claim 15 wherein the undulations in one of the flexible elongate elements having the same direction of rotation and the next adjacent flexible elongate element having the same direction of rotation and having undulations therein offset therein by one cross-over point.

17. A method for enlarging a flow passage extending through an obstruction in a vessel having an inner wall and carrying flowing blood by the use of an expandable flexible cylindrical dilatation member movable between contracted and expanded positions, moving the expandable flexible cylindrical dilatation member into the flow passage in the obstruction while preventing contraction of the flexible cylindrical dilatation member, expanding the flexible cylindrical dilatation member by sufficiently increasing its radial rigidity to compress the obstruction against the inner wall of the vessel to enlarge the flow passage in the obstruction in the vessel while permitting blood to flow through the expandable flexible cylindrical dilatation member during the time the expandable flexible cylindrical dilatation member is in an expanded condition to thereby maintain blood flow in the vessel.

* * * * *